(12) United States Patent
Caserta et al.

(10) Patent No.: US 7,379,662 B2
(45) Date of Patent: May 27, 2008

(54) DEVICE FOR DIFFUSING VOLATILE SUBSTANCES

(75) Inventors: Andrea Caserta, Barcelona (ES);
Cedric Morhain, Barcelona (ES);
David Moreno Perez, Barcelona (ES);
Jose Antonio Muñoz Martinez, Barcelona (ES)

(73) Assignee: Zobele España, S.A., Barcelona (ES)

( * ) Notice: Subject to any disclaimer, the term of this patent is extended or adjusted under 35 U.S.C. 154(b) by 153 days.

(21) Appl. No.: 11/256,077

(22) Filed: Oct. 24, 2005

(65) Prior Publication Data

US 2006/0202050 A1 Sep. 14, 2006

Related U.S. Application Data

(63) Continuation-in-part of application No. 11/073,871, filed on Mar. 8, 2005, now abandoned.

(30) Foreign Application Priority Data

Aug. 2, 2005 (WO) ............ PCT/ES05/00441

(51) Int. Cl.
*F24F 6/08* (2006.01)
*A61L 9/00* (2006.01)
(52) U.S. Cl. .................... 392/395; 239/34; 239/51.5
(58) Field of Classification Search ........... 392/386, 392/390–395; 239/34–51.5
See application file for complete search history.

(56) References Cited

U.S. PATENT DOCUMENTS 2,383,960 A 9/1945 Dupuy
2,412,128 A 12/1946 Coyle
4,413,779 A * 11/1983 Santini ............... 239/45
4,445,641 A * 5/1984 Baker et al. ............ 239/6
4,621,768 A 11/1986 Lhoste et al.
4,739,928 A 4/1988 O'Neil
4,889,286 A 12/1989 Spector
4,913,349 A * 4/1990 Locko ............... 239/34
4,928,881 A 5/1990 Barlics et al.
5,725,152 A 3/1998 Akyu

FOREIGN PATENT DOCUMENTS

| DE | 666593 C | 10/1938 |
| DE | 676131 | 5/1939 |
| EP | 1 088 561 | 4/2001 |
| EP | 1 088 562 A1 | 4/2001 |
| EP | 1 088 561 B1 | 6/2003 |
| ES | 293783 U | 12/1986 |
| ES | 1013796 | 1/1991 |
| ES | 1049393 | 12/2001 |
| GB | 111044 A | 11/1917 |
| GB | 2 371 750 | 8/2002 |
| JP | 2002-200158 A | 7/2002 |
| WO | WO 01/23008 | 4/2001 |

* cited by examiner

*Primary Examiner*—Sang Paik
(74) *Attorney, Agent, or Firm*—McDermott Will & Emery LLP

(57) ABSTRACT

The device for diffusing volatile substances comprises two containers (1, 2) to hold respective liquids with respective volatile substances. Each container has at least one aperture closed by a cap (12, 22). The device is configured so that it can be located on a supporting surface with the containers (1, 2) vertically confronting, so that one of the containers is selectively in an upper position or in a lower position with respect to the other container. The container which is in the upper position emanates the volatile substance which it contains, and the other one does not emanate the volatile substance which it contains.

20 Claims, 9 Drawing Sheets

DEVICE FOR DIFFUSING VOLATILE SUBSTANCES

This application is a continuation-in-part application of U.S. patent application Ser. No. 11/073,871, filed Mar. 8, 2005, incorporated herein for all purposes.

TECHNICAL FIELD OF THE INVENTION

The invention is included in the field of devices for diffusing volatile substances, based on liquids which contain such volatile substances.

BACKGROUND OF THE INVENTION

A broad diversity of devices is known for diffusing fragrances or air-freshening substances, as well as for insecticides, both active (for example, electrical) and passive. The active devices usually have a heater element which heats a solid or liquid material which includes the volatile substance it is desired to diffuse, to evaporate it. The passive devices (or non-electrical) are usually based on the spontaneous evaporation of the volatile substance, for example, by means of evaporation of the same at room temperature.

U.S. Pat. No. 4,739,928 and U.S. Pat. No. 4,621,768 describe passive air-freshening devices of the type of those which incorporate a wick in contact with the air-freshening liquid, which have means to regulate the evaporation of the liquid. U.S. Pat. No. 4,739,928 describes how the adjustment of the emanation of fragrance is achieved through an emanator or absorbent cap coupled to the neck of the container which conforms the air-freshener, by means of a rotational movement of a cover which covers a holder wherein said absorbent cap is housed. U.S. Pat. No. 4,621,768 describes how the regulation of the evaporation of a liquid is achieved by means of some slits arranged in a cover which also rotates, to vary the fragrance-diffusing surface without altering the original form of the apparatus in itself.

U.S. Pat. No. 5,725,152 describes another air-freshener dispenser, which can be used for a long time because the emanator medium is easily replaceable, without prejudice to deforming the air-freshener, to which a special ornamental appearance is given with a cover in the form of a flower.

U.S. Pat. No. 4,928,881 describes a device which contains air-freshening liquid and wick, it being possible to separate the wick and the container of the liquid with respect to the base of the air-freshener which, for its peculiar form can be used for other purposes, such as an ashtray or flowerpot holder, etc.

WO-A-2004/110559 (corresponding to the international patent application no. PCT/ES03/00291) describes an air-freshening device based on the adjustable evaporation of a liquid and which has a cap, to which are incorporated means which prevent it being dismounted from a plug which, on being rotated without the possibility of being extracted from the device, opens the apertures which are present in the plug, exposing a wick impregnated in liquid to the air.

The German patent DE-676131 reflects another system of passive evaporation, based on drops falling from a raised recipient, over evaporation surfaces. The liquid can be collected in a recipient underneath.

ES-U-1013798 describes an air-freshening device in which the substance to evaporate is inside a casing with a generally spherical form which comprises two parts that can be rotated around each other, so that it is possible to vary the size of some orifices or apertures which allow the evaporated substance to pass from the interior of the casing to the exterior.

GB-A-2371750 describes a transparent air-freshening device based on the use of liquids selected so that a change of colour or the like takes place when the active substance to be evaporated has been exhausted.

U.S. Pat. No. 2,412,128 describes a device that can evaporate an active substance when it is positioned "downwards".

EP-A-1088561 describes a number of devices for diffusing volatile substances based on the use of a special wick which acts so that the liquid to evaporate can only be absorbed from a point near to the bottom of the container or reservoir which holds the liquid. Thus, if the reservoir is positioned "downwards", no evaporation of the liquid takes place. This allows configurations to be implemented with several containers or reservoirs which can hold different volatile active substances, and wherein the substance to evaporate is chosen by positioning the corresponding container "upwards".

U.S. Pat. No. 4,889,286 describes an air-freshener in which a vessel, which holds a liquid which contains the volatile substance it is desired to diffuse, can be located selectively "upwards" or "downwards", the vessel having a cap with vent holes covered by a membrane of a material with micropores. Thus, when the container is upright, the liquid is not in contact with the membrane, and the membrane serves as a barrier to prevent the volatile substances (present inside the container) from discharging to the exterior. When the container is inverted, the liquid rests on the membrane and impregnates the pores or micropores, whereby the volatile substances can pass into the atmosphere. Thus, it can be said that the device is in the active or ON state when the container is located with its face downward, and in a non-active or OFF state when the container is with its face upward.

As for the active evaporation devices, a great number of the same is to be found which describe systems based on an electric heater element. ES-U-1049393 describes a system of this type which includes a box in which several electric evaporators are located. The system is configured so that it is possible to program selective connection and disconnection of the evaporators and thereby achieve an overall evaporation intensity, uniform in time.

SUMMARY OF THE INVENTION

It has been considered that interest exists in a device with which it is possible to selectively diffuse different volatile substances, which the user can operate easily and which can be manufactured with a reduced number of different pieces.

The invention relates to a device for diffusing volatile substances which comprises two containers to hold respective liquids (which can contain respective different volatile substances, for example, different types of air-fresheners and/or insecticides). Each container has at least one aperture closed by a cap. The device is configured so that it can be located on a supporting surface with the containers vertically confronting, so that one of the containers is selectively in an upper position or in a lower position with respect to the other container, so that one of the containers is in said upper position and the other of the containers is in said lower position, at the election of the user. The containers are oriented in the device so that the container which is in the upper position has its aperture downwards, and so that the container which is in the lower position has its aperture upwards.

Each cap is configured so that it allows the passage of a volatile substance contained in the liquid in the container into the surrounding atmosphere when the cap is in contact with the liquid, and so that it does not allow the passage of said volatile substance into the surrounding atmosphere when the cap is not in contact with the liquid. Thus, the container which is in the upper position is in state of emanating the volatile substance ("on"), and the container which is in the lower position is in state of not emanating the volatile substance ("off"). This is very practical, since, for example, it allows the level of consumption to be seen from above. Also, it is a friendly and intuitive system for the user, and the user can choose which active substance to diffuse (for example, choose between an air-freshener and an insecticide), by simply turning the device through 180 degrees, positioning the "active" container upwards. Also, this configuration allows a possible label of the content of the container associated with the corresponding container to be easily read—for example, a label stuck on the container—, whereby the user can always see which substance is being diffused.

Optionally, the device can comprise a cover element located between the apertures of the two containers and movable with respect to said apertures, so that said cover element rests by gravitational force on the aperture of the container which is in the lower position, forming a barrier against the evaporation of volatile substances from the cap of said container which is in the lower position. In this way it is achieved that, by turning the device around, the container which becomes the lower one ceases forthwith to emit the volatile substances, even in the event that the cap is still impregnated with the liquid. Also, the cover element can serve to absorb a certain leakage from the container which is in the upper position.

The cover element can comprise at least one part of a liquid-absorbing material, to absorb such possible leakage of liquid from the container which is in the upper position. The cover can, for example, be made of a material such as plastic or similar and have this absorbent material on its supporting or similar surfaces.

The cover element can be substantially planar and comprise one or several rims which projects with respect to a substantially planar surface of said cover element. These rims can be configured to surround a salient area of the respective container, in correspondence with the cap of the container, in order to better effect the sealing or barrier action against the evaporation from the cap of the container which is in the lower position.

Each cap can be of a material which has micropores so that a liquid can penetrate into said micropores from an internal surface of the cap, so that evaporation takes place of at least a part of said liquid on an external surface of the cap. For example, a material can be used like that described in U.S. Pat. No. 4,889,286.

The cap can, for example, be made of sintered polyethylene. This material has a certain porosity, whereby it can be impregnated with a liquid when it is in contact with the liquid, and allows evaporation of the liquid to take place from an external surface of the cap. Likewise it can form a barrier against evaporation when it is not in contact with the liquid.

Each cap can have, on an external surface with respect to the corresponding container, a plurality of cylindrical or similar projections to facilitate the evaporation of a liquid that soaks the cap on the external surface (through the effect of increasing or multiplying the evaporation surfaces).

The device additionally can comprise a supporting structure, with the containers mounted in said supporting structure.

The supporting structure can comprise two ring-shaped elements (for example, of plastic), with one side configured to receive the respective container and with the other side configured to be coupled to the other ring-shaped element. Each ring-shaped element additionally can comprise, in correspondence with the side configured to receive the respective container, a plurality of flexible projections configured to fit in at least one corresponding notch in the container.

Each ring-shaped element can comprise, in correspondence with the side configured to be coupled to the other ring-shaped element, a plurality of projections and recesses complementary to projections and recesses of the ring-shaped other element and configured so that the ring-shaped elements can be coupled so that they are retained by each other, with the possibility of one ring-shaped element turning with respect to the other one.

Each ring-shaped element can be configured so that with the ring-shaped elements coupled to each other, and with the containers mounted in the respective ring-shaped elements, an interior space is established defined by the containers and by the ring-shaped elements, the caps of the containers being located in correspondence with said interior space. Thus, the volatile substances pass from the containers to the interior space, and from there to the external space. Thus, a system of access regulation can be established between the interior space and the exterior, in order to regulate the degree of diffusion of the volatile substances. Also, this configuration allows a restricted access to be established to the interior space: by selecting the dimensions and configuration of the elements appropriately, it is possible to manage that the user does not have manual access to the interior space or, at least, that such access is not easy for him. Thus, it is possible to ensure that the user cannot easily access elements liable to have been in direct contact with the liquid or with the volatile substance which it is desired to diffuse, a feature which makes the device specially attractive from a health and safety point of view.

For example, the ring-shaped elements can be configured so that they establish at least one access window to said interior space, and so that said at least one window is of a size which can be varied by rotating one of the ring-shaped elements with respect to the other, so that said window constitutes a means of regulation for the egress of a volatile substance from said interior space into the surrounding atmosphere. For example, the ring-shaped elements can be configured so that they establish at least two of said windows. The use of this window or windows not only serves to establish a means of regulating the diffusion, it also allows the access to the interior space to be limited, for example, by selecting the dimensions of the window or windows so that a user cannot introduce his fingers into the interior space. Thus, a safe and hygienic device is obtained which does not allow the user to access the parts liable to have been in direct contact with the volatile substance to be diffused or with the liquid which contains it.

That is, the window or windows can be of a size such that a user cannot have access with his hand (for example, with the fingers) to the interior space and especially so that he cannot touch the caps or the surfaces of the cover element, which elements are liable to have been in direct contact with the volatile substance or to be impregnated with the liquid which contains it.

The two ring-shaped elements can be identical, which reduces the number of different pieces necessary for the manufacture of the device.

Each container can comprise, in correspondence with its aperture, a sealing element which covers the cap to prevent evaporation taking place of the volatile substance prior to the withdrawal of the sealing element. This sealing element can have a part configured to project through said at least one window, so that the sealing element can be withdrawn with the containers mounted in the respective ring-shaped elements, by pulling on the part which projects through the window. This allows said sealing element to be withdrawn without the user having to access the interior space, a feature which can be advantageous from a health and safety point of view and.

The device can have a substantially spherical configuration, with a substantially planar supporting area on each container, so that the device can be located in a substantially stable position on a planar supporting surface, with one container selectively in an upper or lower position with respect to the other one, at the option of the user.

Each container can have a part in the form of a spherical cap, with said supporting area located in a central area of the surface of said spherical cap.

The two containers can be identical, which reduces the number of different pieces necessary for the manufacture of the device.

The containers can be made of, for example, glass.

DESCRIPTION OF FIGURES

To complete the description and with the object of assisting in a better understanding of the characteristics of the invention, in accordance with a preferred practical embodiment thereof, accompanying said description as an integral part thereof, is a set of drawings wherein, by way of illustration and not restrictively, the following has been represented.

DETAILED DESCRIPTION OF THE INVENTION

Figure 1:
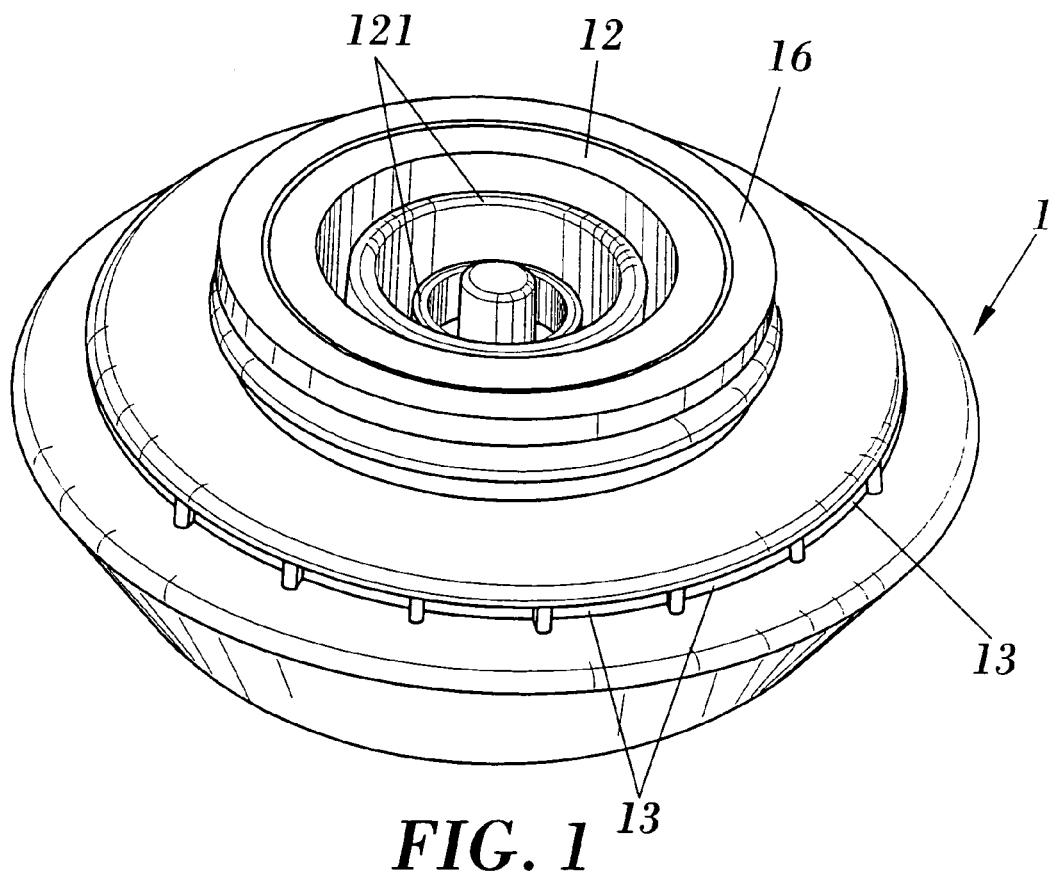
FIG. 1. It shows a view in perspective of a container for a device in accordance with a preferred embodiment of the invention.

FIG. 1 shows a container which is part of a possible embodiment of the invention, which comprises two of these containers. Container 1 is made of glass, a feature which gives an appearance of high quality, although it is also possible to use any other appropriate material.

Figure 2:
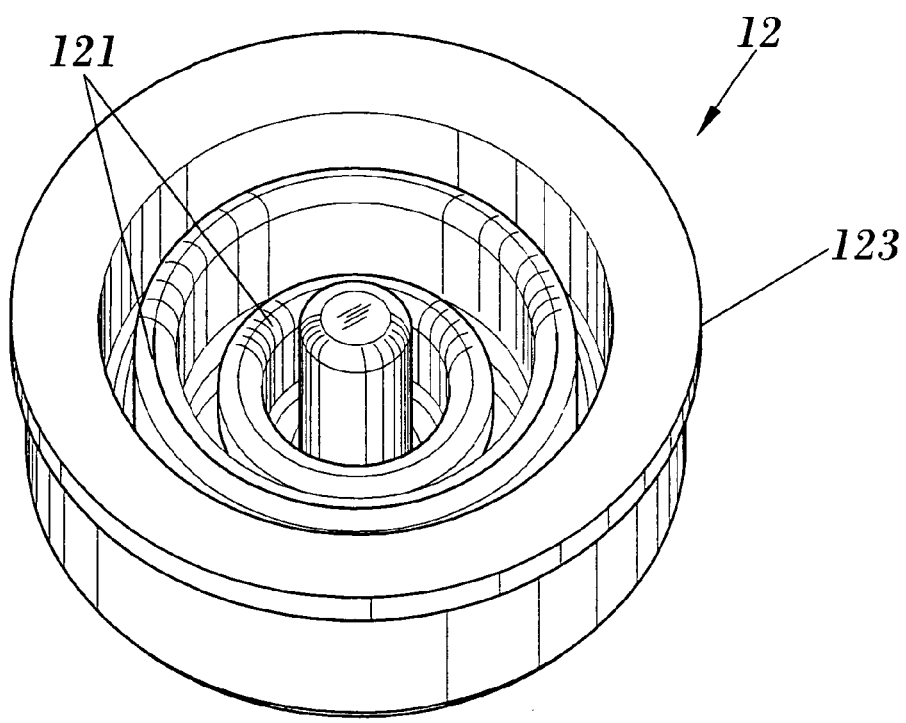
FIG. 2. It shows a view in perspective of the external part of a cap in accordance with a preferred embodiment of the invention.

In FIG. 1 the part of the container is observed which is "inside" the device, and which comprises a plurality of notches 13 into which some flexible projections will be inserted which form part of the ring-shaped elements of the supporting structure and which serve to retain container 1 in said supporting structure. Furthermore, it is observed how the container has a cylindrical projecting part 16 which defines the aperture in which a cap 12 made of sintered polyethylene or of another microporous material is inserted which allows a liquid to pass through the material when it is in direct contact with the material, so that it is possible to produce, on an external surface of the material, evaporation of a volatile substance. On the other hand, when the container is located with the aperture upward, as in FIG. 1, the liquid contained in the container is not in contact with the cap and so the cap acts as a barrier and does not allow the volatile substances which are present in the container, to pass into the surrounding atmosphere. That is, the cap then has a barrier function. The cap, on its external surface, has a plurality of cylindrical projections 121 which serve to increase the effective size of the evaporation surface (see also FIG. 2). The cap also has, in correspondence with its external part, a peripheral rim 123 upon which a corresponding configuration in the container is seated.

Figure 3:
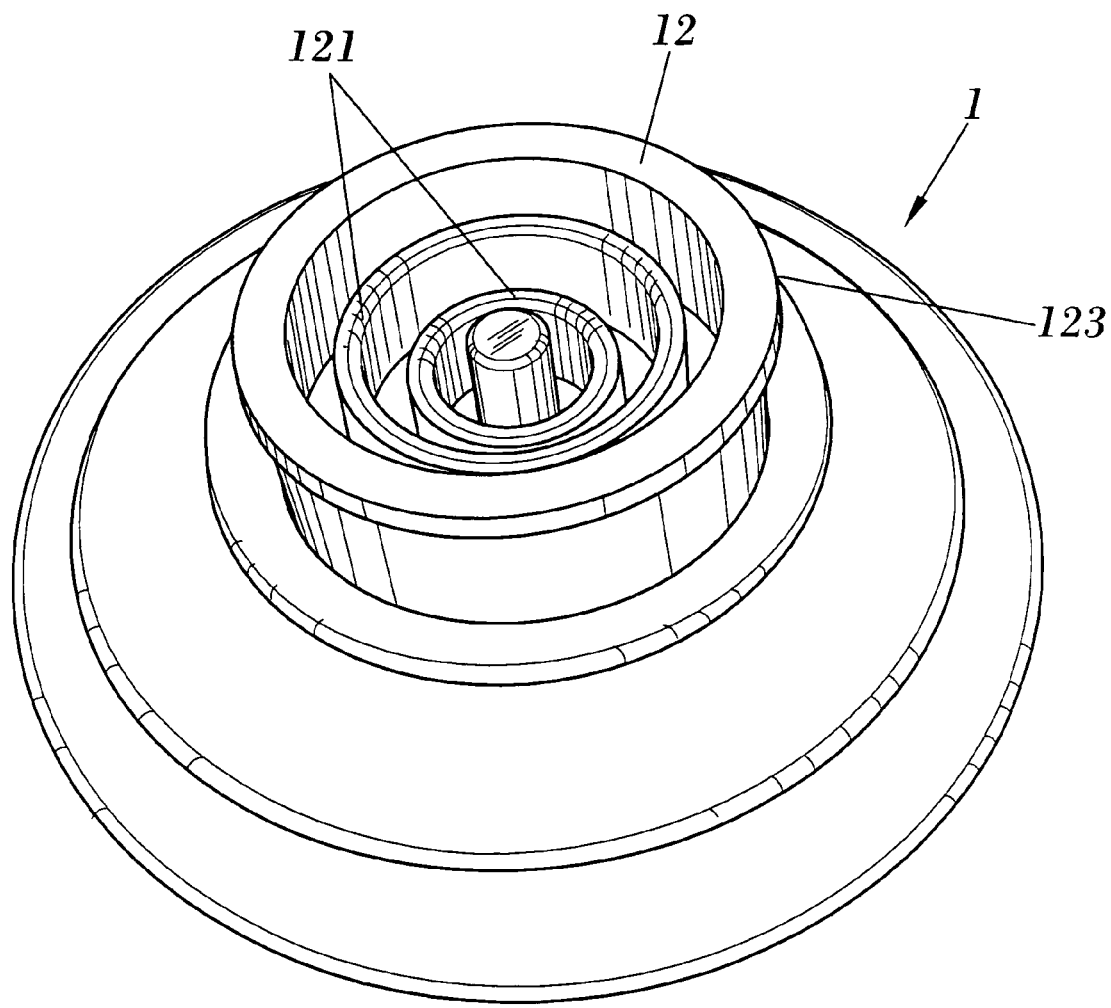
FIG. 3. It shows a view in perspective of the cap partially inserted in the container.

FIG. 3 shows a view in perspective of the cap 12 partially inserted in container 1.

In use, the container is filled with a liquid which contains the volatile substance or the volatile substances to be evaporated. Thus, and due to the way in which the cap works, the evaporation and passage to the exterior of the substance can take place when the container is located with the liquid in contact with the cap, and does not take place when the cap is not in contact with the liquid, that is, when it is located with the aperture and cap upward (however, when the container is changed from a position in which the aperture is downward to a position in which the aperture is upward, it is possible that evaporation continues to take place of the liquid which is at that moment soaked in the cap).

Figure 4:
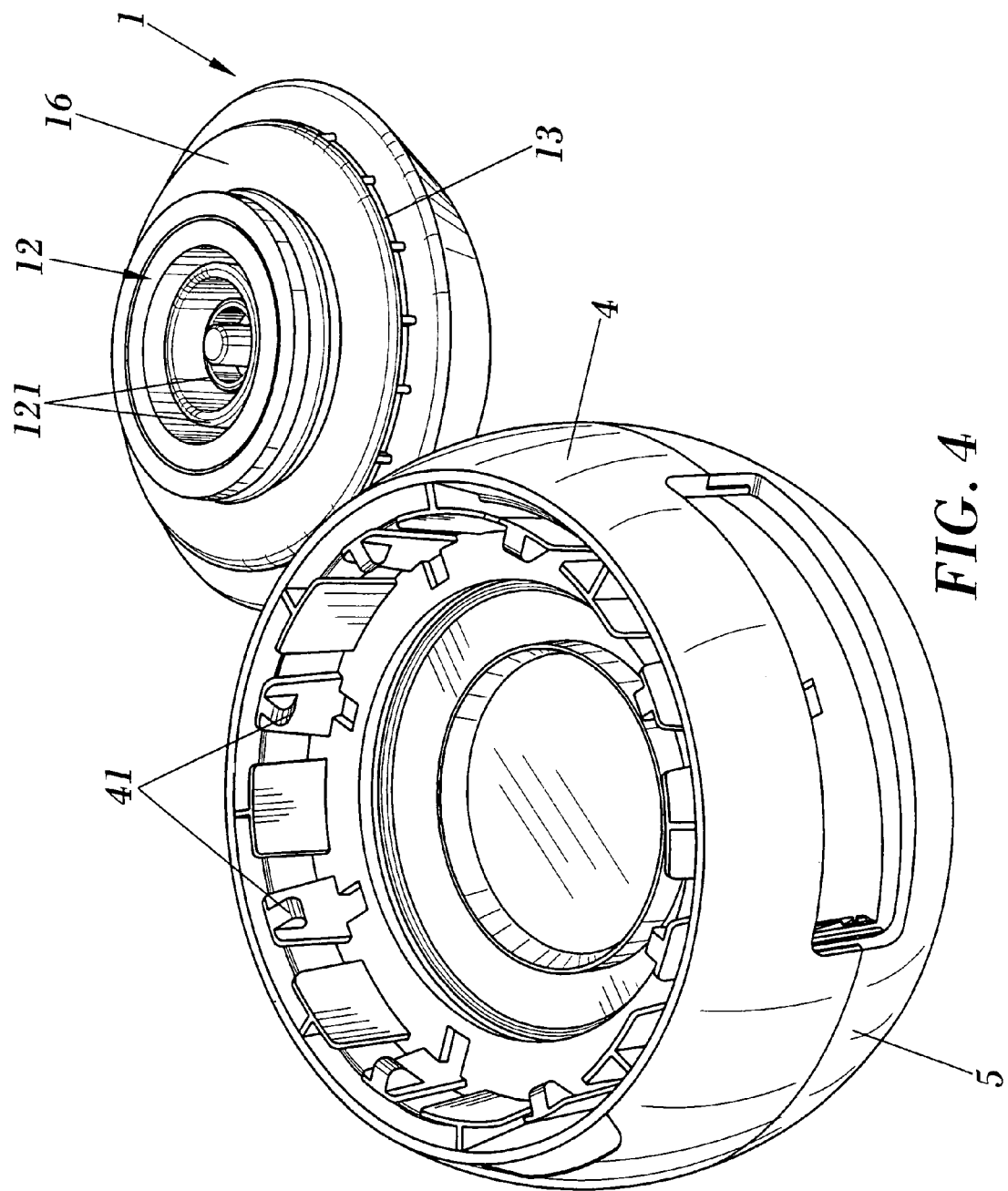
FIG. 4. It shows a view in perspective of a container and of a supporting structure.

FIG. 4 illustrates schematically a supporting structure which comprises two ring-shaped elements 4 and 5, joined to each other, as well as container 1 with notches 13. As can be observed, container 1 can be inserted in the upper orifice of the ring-shaped element 4, with the cap facing inward (downward in FIG. 4). So, the ends of flexible projections 41 in the upper part of ring-shaped element 4 are inserted in notches 13 of container 1, so that container 1 is retained in the ring-shaped element 4. In like manner, another container can be introduced and retained in the other ring-shaped element 5.

Figure 5:
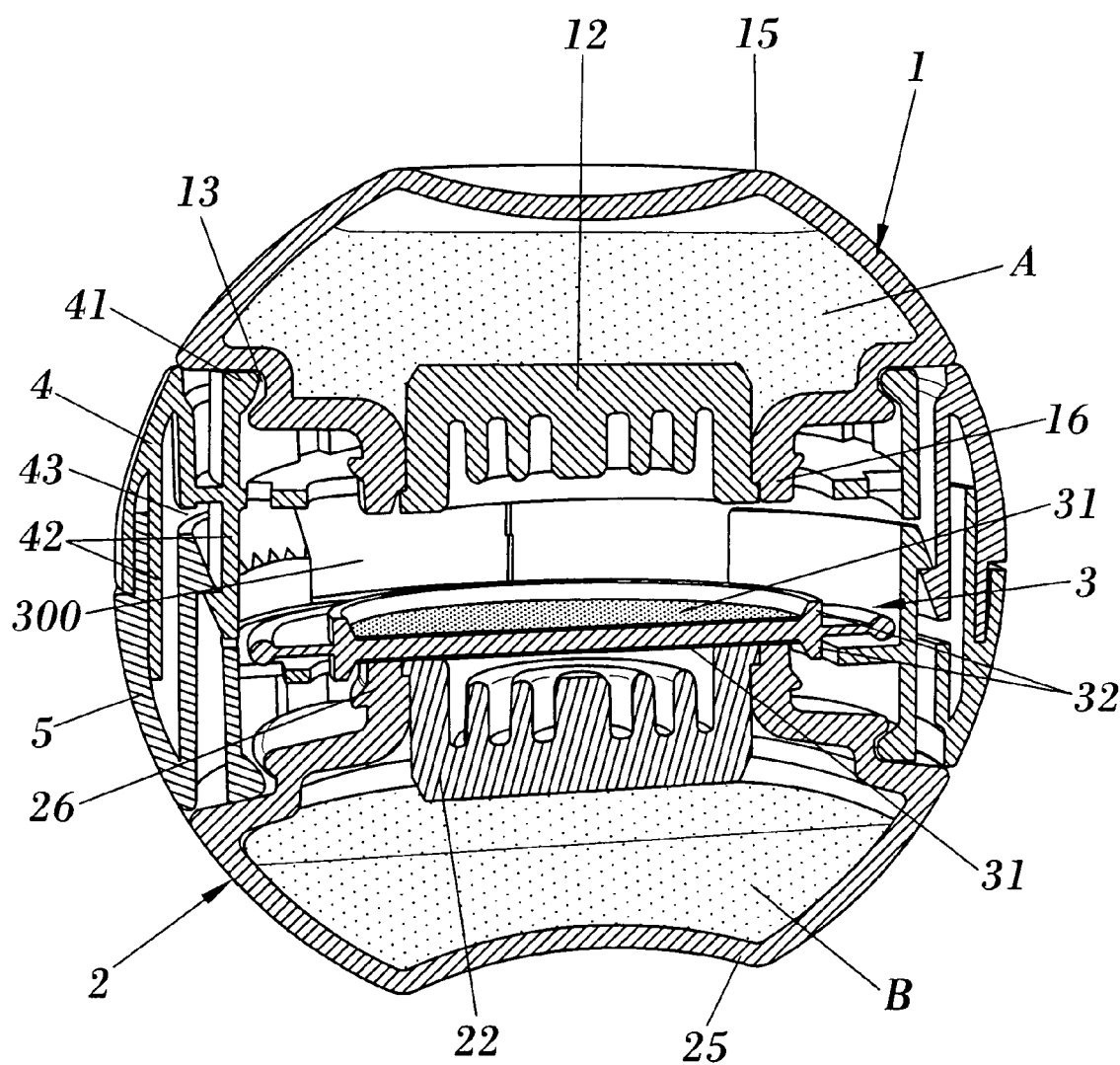
FIG. 5. It shows a view in cross section of a device in accordance with this preferred embodiment of the invention.

In FIG. 5 the mounted device can be observed in cross section. The device comprises the two containers 1, 2 with their corresponding caps 12, 22 mounted in the projecting parts 16, 26. Each container is mounted in one of the two ring-shaped elements 4, 5 which constitute the support and which retain the containers with flexible projections 41, the ends 13 of which enter into the corresponding notches in the containers, as has been described above.

The two ring-shaped elements 4 and 5 are mutually mated by means of a system of recesses 43 and projections 42 as is illustrated schematically in FIG. 5. The ends in transversal projection of some of these projecting elements produce an axial coupling of the two ring-shaped elements 4, 5, whereby they remain joined but able to turn with respect to each other (this type of joined structure is in itself conventional, and a great number of spherical devices exists which present this type of structure to maintain two parts joined to each other, but able to turn; for this reason, it is not considered necessary to describe this structure in greater detail). The structure has an interior space 300 wherein the caps 12, 22 of the two containers are confronting each other.

As can be observed in FIG. 5, one of the containers contains a liquid A which can contain a first volatile substance (or combination of volatile substances), and the other container holds a liquid B with another volatile substance (or combination of volatile substances). The device is located over a planar supporting area 25 of the spherical cap of the lower container 2, which area has a substantially annular form in the supporting plane. The other container has a corresponding supporting area 15 on its spherical cap.

In the position of the device illustrated in FIG. 5, container 2 which is in the lower position does not have the cap in contact with liquid B, for which reason cap 22 acts as a barrier and does not allow the volatile substances present inside container 2 to pass to the interior space 300 of the device. On the other hand, liquid A which is in container 1 which is in the upper position is in direct contact with cap 12 of said container, whereby it is soaking said cap, whereby the corresponding volatile substance passes to the external surface of the cap, where it evaporates and passes into the interior space 300, to then pass to the exterior of the device through windows which will be discussed below.

Moreover, it is observed how the device contains, in the interior space and between the two containers, a cover element 3 which is resting on the aperture of lower container 2, by gravity. This cover element 3 has a substantially planar configuration 3 with a surface which has two rims 32 (one upper and another lower in FIG. 5) which serve to surround the projecting area 16, 26 corresponding to the aperture of the corresponding container. In this way, the cover element always rests on the aperture and cap of the container which is in the lower position, and prevents an emanation of volatile substances taking place from the residual liquid which could be present in the cap (in this manner it is possible to achieve an immediate interruption of the emanation of the volatile substances when a container passes from the upper position to the lower position, without needing to wait for the liquids to evaporate which are soaking the cap).

Also, cover element 3 is fitted with a part 31 of a liquid-absorbing material, to absorb any possible leakage of liquid from the container which is in the upper position. Usually, such a leakage should not take place, but it is possible that, for example, with increasing temperatures in the surroundings in which the device is located, the pressure inside the container increases, which can produce a leak. The part of absorbent material 31 serves to ensure that the user can never come into contact with the drops, since they are retained in the cover element. The cover element can, for example, be made of plastic and have an element of absorbent material located in the central part defined by rim 32.

Figure 6A:
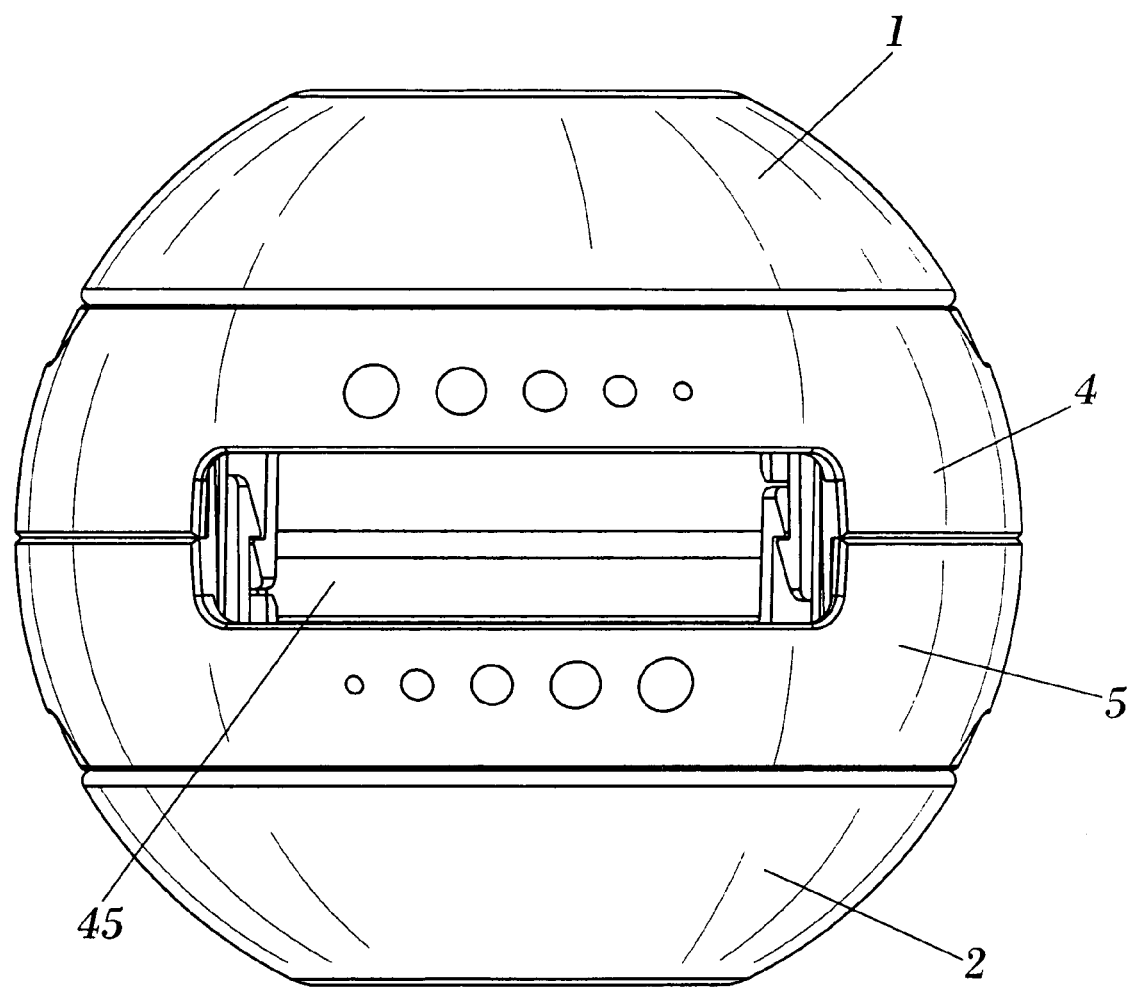
FIGS. 6A-6C. They show schematic views in side elevation of the device in accordance with this preferred embodiment of the invention, in different stages of turning between the ring-shaped elements.
Figure 6B:
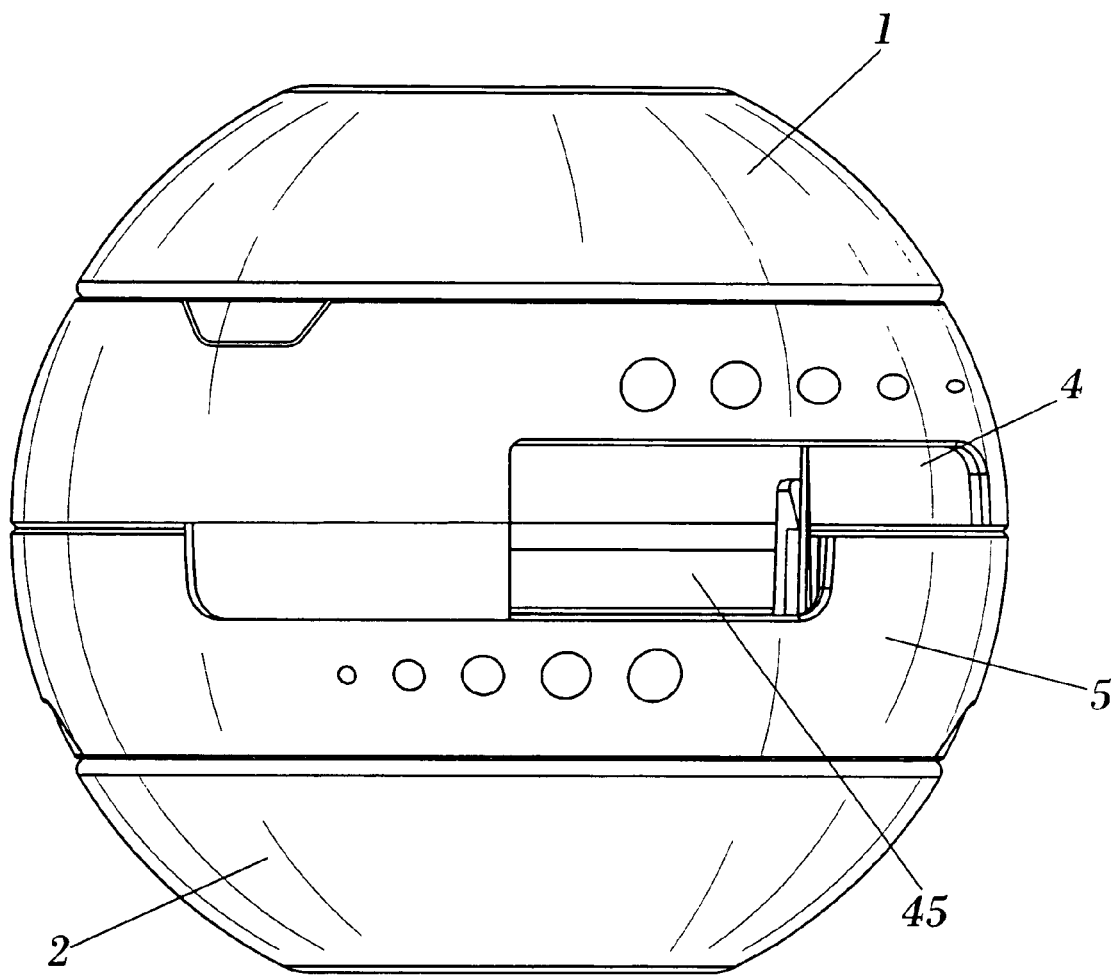
Figure 6C:
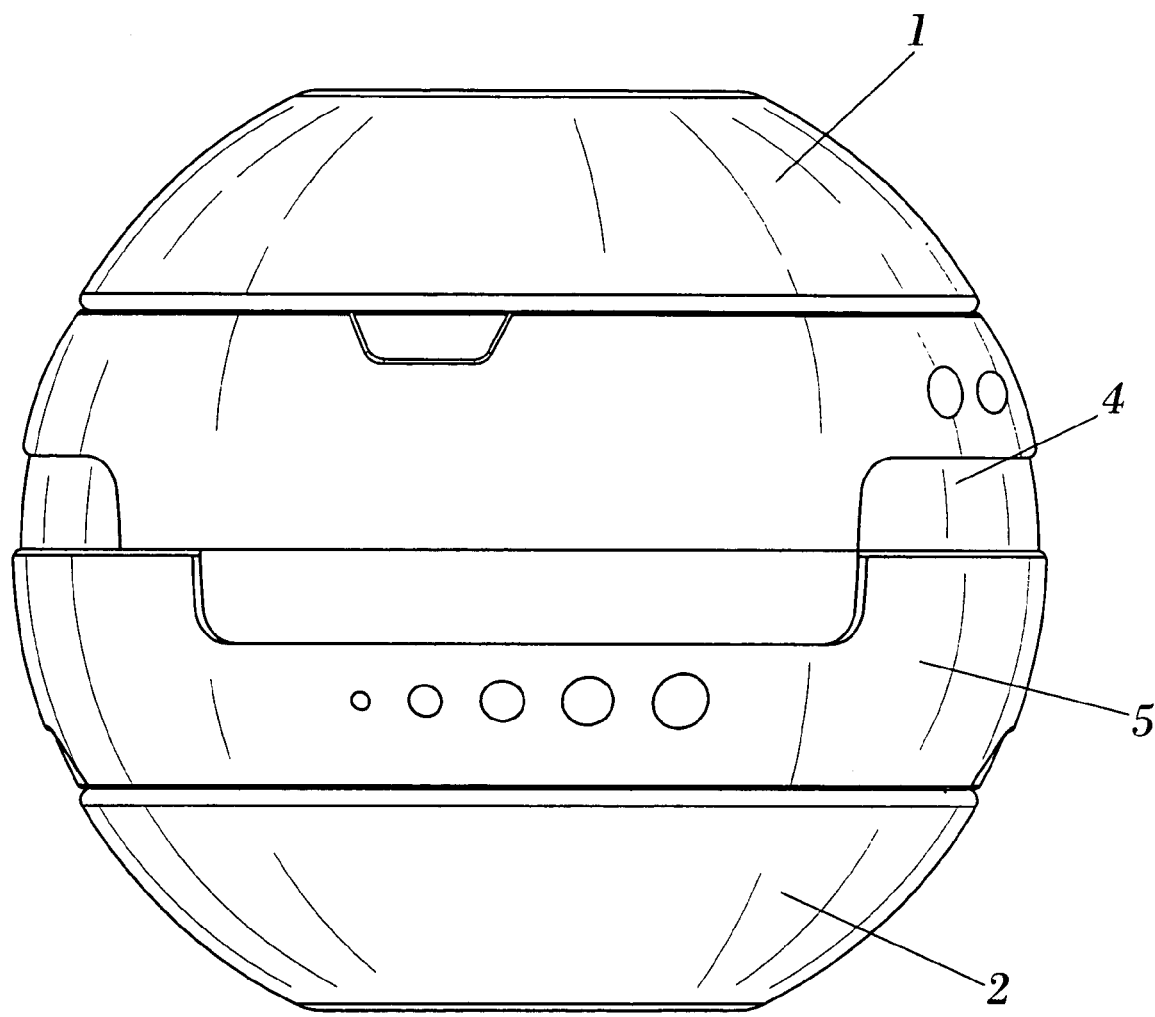

If the user of the device illustrated in FIG. 5 wishes to change the current dispersion of the active substance of liquid A to dispersion of the active substance of liquid B, he can simply take the device and turn it through 180 degrees, with which it will be resting on supporting surface 15. In such a case, cover element 3 will be resting on projecting part 16 of container 1 which has changed to being in the lower position, and immediately interrupts the emanation of the volatile substances of cap 12 (independently of whether said cap continues to be soaked in liquid A). At the same time, it frees projecting part 26 of the other container, at the same time as cap 22 of said container is soaked in liquid B, whereby the corresponding volatile substances can pass to the interior space 300 of the device, and from there to the exterior, through windows 45 foreseen in the supporting structure and which are illustrated in FIGS. 6A-6C.

The ring-shaped elements 4, 5 are configured so that they establish two windows 45 of access to the interior space (from the exterior) (and vice versa). Each window 45 is of a size which is varied by rotating one of the ring-shaped elements 4 with respect to the other one 5. Thus, the windows 45 constitute a general means of regulating the egress of a volatile substance from said interior space to the exterior. FIG. 6A shows one of these windows 45 in its state of maximum openness, FIG. 6B shows the window partially closed, and FIG. 6C shows the window completely closed (in which case the passage of the volatile substances is impeded from the interior space 300 to the exterior). The windows can be of a size so that a user cannot introduce his hand (for example, the fingers) through the window and touch the caps 12 or 22 or the surfaces of the cover element 3.

Figure 7:
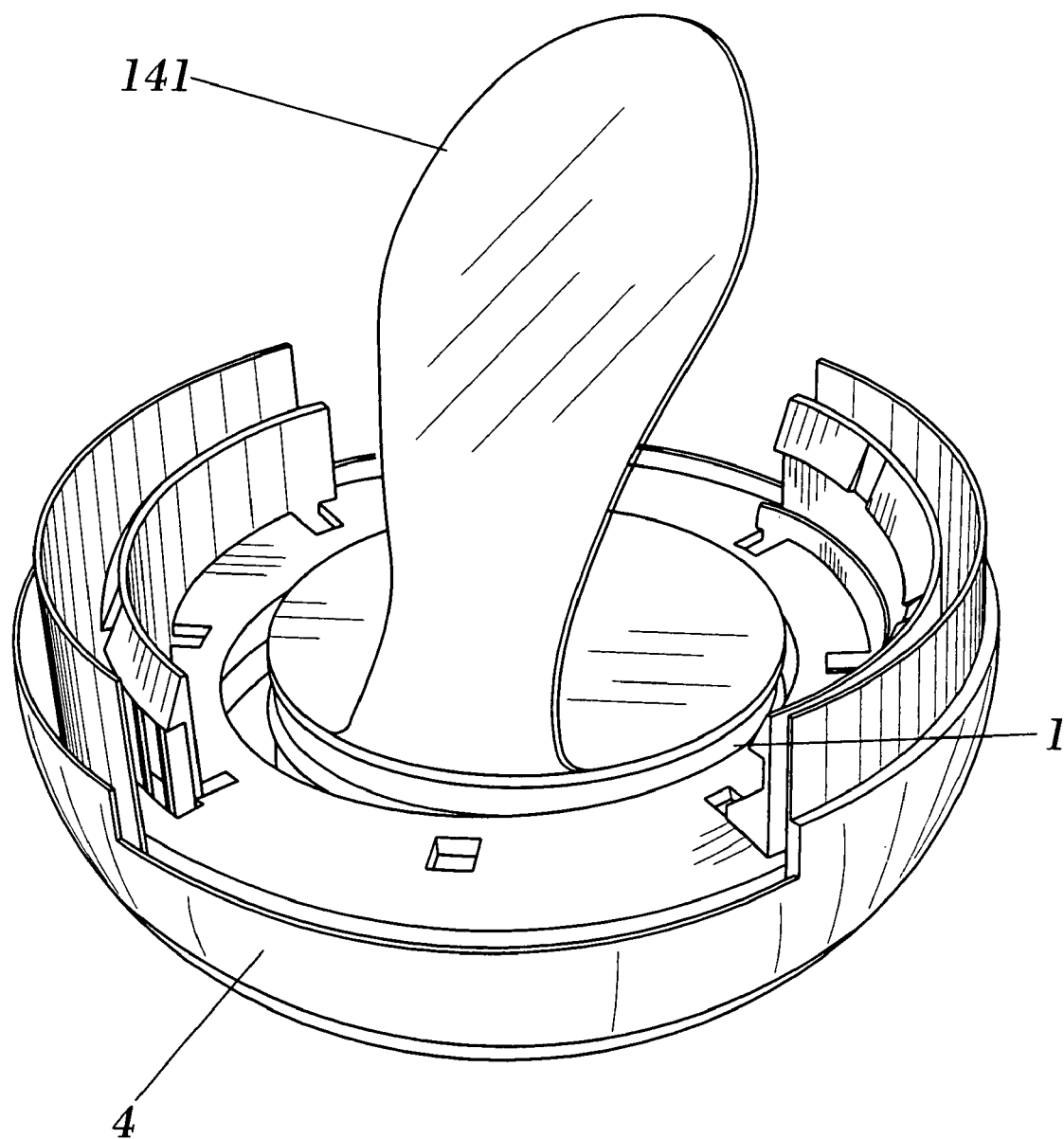
FIG. 7. It shows a view in perspective of a container with a sealing element.

In FIG. 7 it is observed how the container has its cap covered externally with a laminar sealing element 14, which has an elongated part 141. Said sealing element establishes an external hermetic closure of the container, and prevents the liquid from evaporating before the sealing element is withdrawn. As is habitual in this type of diffusion device, this element is stuck to the container and/or the cap with an adhesive means or similar, and is easily withdrawn by pulling on the part 141 which is projecting. In this case, this part is elongated so that it can project through the window, so that a user can remove the sealing element from outside, without dismantling the device. Thus, the device is very hygienic, since any part liable to be impregnated by one of the liquids contained in the containers is out of the user's reach.

Figure 8:
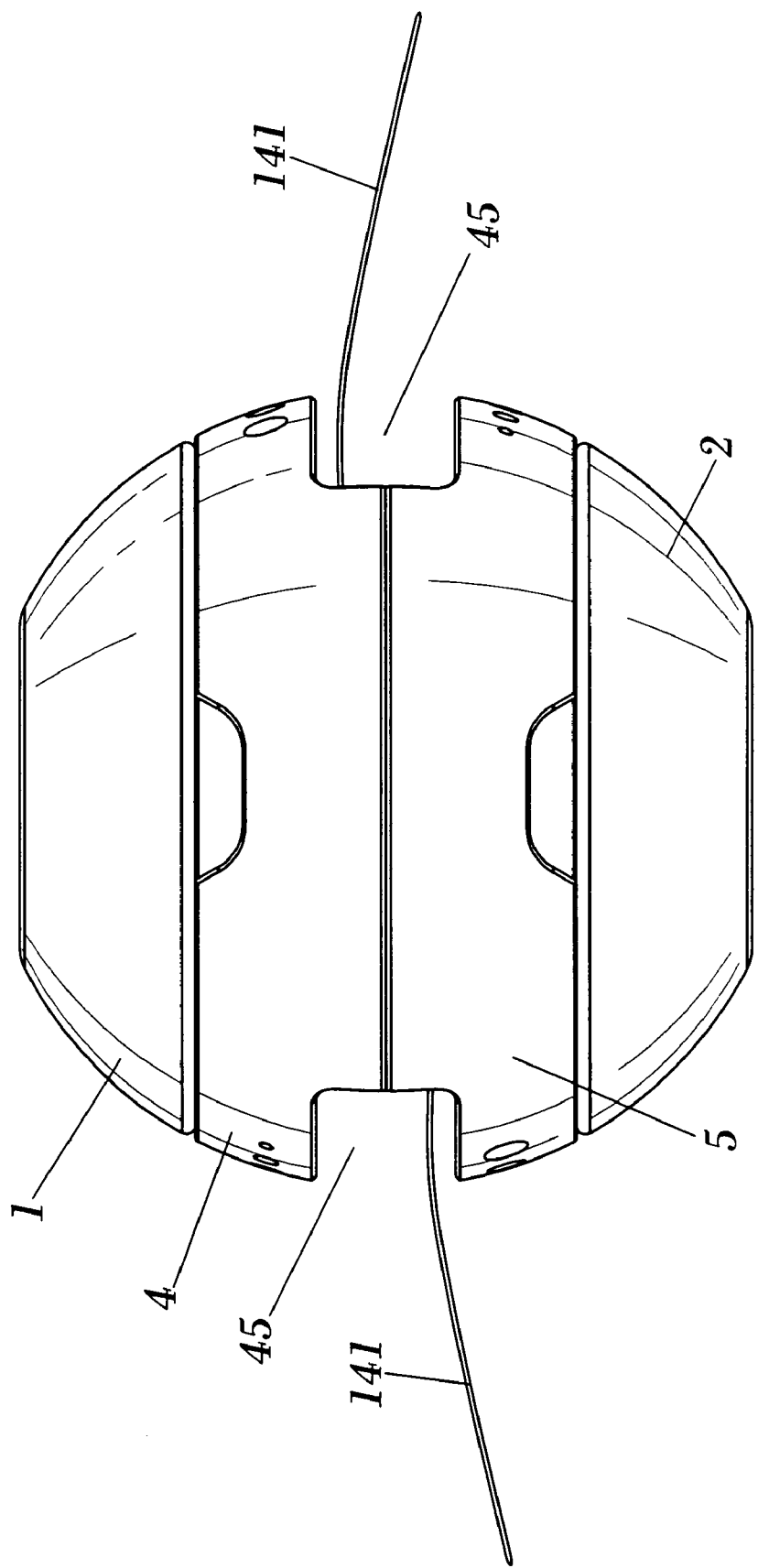
FIG. 8. It shows a schematic view of the device with parts of two sealing elements projecting through the windows.

FIG. 8 illustrates schematically the configuration in which the elongated parts 141 of individual sealing elements corresponding to respective containers project from respective windows 45 of the device. Logically, it is also possible that these parts of the sealing elements emerge to the exterior through a same window.

The device described can be manufactured with a reduced number of pieces: two identical containers with their identical caps, two identical ring-shaped elements and a cover element. That is, it only requires 4 types of element: cap, container, ring-shaped element and cover element. Logically, this facilitates production and logistics.

In this text, the word "comprises" and its variants (such as "comprising", etc.) should not be interpreted in an exclusive manner, that is to say, they do not exclude the possibility that what is described include other elements, steps, etc.

Moreover, the invention is not limited to the specific embodiments which have been described but also includes, for example, the variants which can be implemented by the average expert in the matter (for example, with regard to the selection of materials, dimensions, components, configuration, etc.), within that which is deduced from the claims.

The invention claimed is:

1. A device for diffusing volatile substances, comprising:
   two containers configured to hold respective liquids with respective volatile substances, each container having at least one aperture closed by a cap, wherein each cap is configured to allow the passage of the volatile substance contained in the liquid into the surrounding atmosphere when the cap is in contact with the liquid, and further configured to prevent the passage of the volatile substance into the surrounding atmosphere when the cap is not in contact with the liquid; and a supporting structure configured to mount the two containers therein, the supporting structure comprising two support elements, wherein each support element comprises a first side configured to receive a respective one of the two containers and a second side configured to be coupled to the other support element, wherein the device is configured to be located on a supporting surface with the containers vertically confronting, wherein one of the containers is selectively in an upper position with respect to the other container in a lower position, the one container which is in the upper position having its aperture downward and in a state of emanating the volatile substance in the container, and the other container which is in the lower position having its aperture upward and in a state of not emanating the volatile substance in the container.

2. The device in accordance with claim 1, further comprising a cover element located between the apertures of the two containers and movable with respect to said apertures, wherein the cover element rests by gravity on the aperture of the container which is in the lower position, acting as a barrier against the evaporation of volatile substances from the cap of the container which is in the lower position.

3. The device according to claim 2, wherein the cover element comprises at least one part of a liquid-absorbing material configured to absorb a possible leakage of liquid from the container which is in the upper position.

4. The device according to claim 2, wherein the cover element is substantially planar and comprises at least one rim which projects with respect to a substantially planar surface of said cover element and which is configured to surround a projecting area of the respective container, corresponding to the cap of the container.

5. The device according to claim 1, wherein each cap is made of a material which has micropores so that a liquid can penetrate into said micropores from an internal surface of the cap, so that evaporation takes place of at least a part of said liquid on an external surface of the cap.

6. The device according to claim 1, wherein each cap is made of sintered polyethylene.

7. The device according to claim 1, wherein each cap has, on an external surface with respect to the corresponding container, a plurality of cylindrical projections.

8. The device according to claim 1, wherein each support element comprises, in correspondence with the side configured to receive the respective container, a plurality of flexible projections configured to fit in at least one corresponding notch in the container, to retain the container.

9. The device according to claim 1, wherein each support element comprises, in correspondence with the side configured to be coupled to the other support element, a plurality of projections and recesses complementary to projections and recesses of the other support element and configured so that the support elements can be coupled so that they are retained by each other, with the possibility of turning one support element with respect to the other one.

10. The device according to claim 9, wherein each support element is configured so that with the support elements coupled to each other, and with the containers mounted in the respective support elements, an interior space is established, defined by the containers and by the support elements, the caps of the containers being located in correspondence with said interior space.

11. The device according to claim 10, wherein the support elements are configured so that they establish at least one window of access to said interior space from the exterior, and so that said at least one window is of a size which can be varied by rotating one of the support elements with respect to the other, so that said window constitutes a means of regulating the egress of a volatile substance from said interior space into the surrounding atmosphere.

12. The device according to claim 11, wherein the support elements are configured so that they establish at least two of said windows.

13. The device according to claim 1, wherein the two support elements are identical.

14. The device according to claim 11, wherein each container comprises, in correspondence with its aperture, a sealing element which covers the cap to prevent evaporation taking place of the volatile substance prior to withdrawal of the sealing element, said sealing element having a part configured to project through said at least one window, so that the sealing element can be withdrawn with the containers mounted in the respective support elements, by pulling on said part configured to project through said window.

15. The device according to claim 1, which has a substantially spherical configuration, with a substantially planar supporting area on each container, so that the device can be located in a substantially stable position on a planar supporting surface, with one container selectively in an upper or lower position with respect to the other one.

16. The device according to claim 15, wherein each container has a part in the form of a spherical cap, with said supporting area located in a central area of the surface of said part in the form of a spherical cap.

17. The device according to claim 1, wherein the two containers are identical.

18. The device according to claim 1, wherein the containers are made of glass.

19. The device according to claim 1, wherein the two support elements of the supporting structure are ring-shaped.

20. The device according to claim 1, wherein each support element comprises, in correspondence with the side configured to be coupled to the other support element, a plurality of projections and recesses complementary to projections and recesses on the other support element and is configured to retain the other support element, wherein each support element is turnable with respect to the other support element.

* * * * *